United States Patent [19]

Maruyama et al.

[11] Patent Number: 4,599,455
[45] Date of Patent: Jul. 8, 1986

[54] PROCESS OF PURIFYING FLUORINATED CARBONYL COMPOUND MIXED WITH HYDROGEN FLUORIDE

[76] Inventors: Yutaka Maruyama, No. 1-6-8, Minami-dai, Kamifukuoka City; Junji Negishi, No. 1-10-24, Suna-shinden, Kawagoe City; Katuyoshi Murata, No. 1-6-8, Minami-dai, Kamifukuoka City; Yutaka Katsuhara, No. 4-18-7, Suna-shinden, Kawagoe City, all of Japan

[21] Appl. No.: 604,534

[22] Filed: Apr. 27, 1984

[30] Foreign Application Priority Data

Apr. 30, 1983 [JP] Japan .................. 58-74925

[51] Int. Cl.$^4$ ............ C07C 45/78; B01D 53/14
[52] U.S. Cl. .................. 568/411; 568/492; 203/42; 55/71; 423/488
[58] Field of Search .......... 203/29, 28, 35, 33, 203/50, 42; 55/71, 68; 568/411, 410, 492, 394, 490, 466; 423/483, 484, 488

[56] References Cited

U.S. PATENT DOCUMENTS

| | | | |
|---|---|---|---|
| 3,358,033 | 12/1967 | Anello et al. | 568/411 |
| 3,406,099 | 10/1968 | Buckman et al. | 568/411 |
| 3,433,838 | 3/1969 | Cunningham et al. | 568/411 |
| 3,544,633 | 12/1970 | Yodis et al. | 568/411 |
| 3,632,652 | 1/1972 | Chu et al. | 568/411 |
| 3,745,093 | 7/1973 | Lee | 568/411 |
| 4,059,633 | 11/1977 | Childs | 568/411 |
| 4,473,712 | 9/1984 | Bonfield et al. | 568/411 |

FOREIGN PATENT DOCUMENTS 42-10202 6/1967 Japan .

Primary Examiner—Wilbur Bascomb

[57] ABSTRACT

A fluorinated carbonyl compound

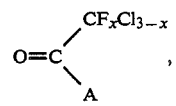

where x is 2 or 3 and A represents $CF_3$ or H, coexisting with hydrogen fluoride in a mixed gas is purified by first adjusting the temperature of the mixed gas to 100°–300° C. to cause decomposition of a usually coexisting complex of the fluorinated compound with HF and then bringing the hot mixed gas into contact with concentrated sulfuric acid maintained at 10°–40° C. Almost the entire amount of HF is absorbed in sulfuric acid and subsequently recovered, while the purified compound neither dissolves in sulfuric acid nor reacts with HF present in sulfuric acid.

5 Claims, 1 Drawing Figure

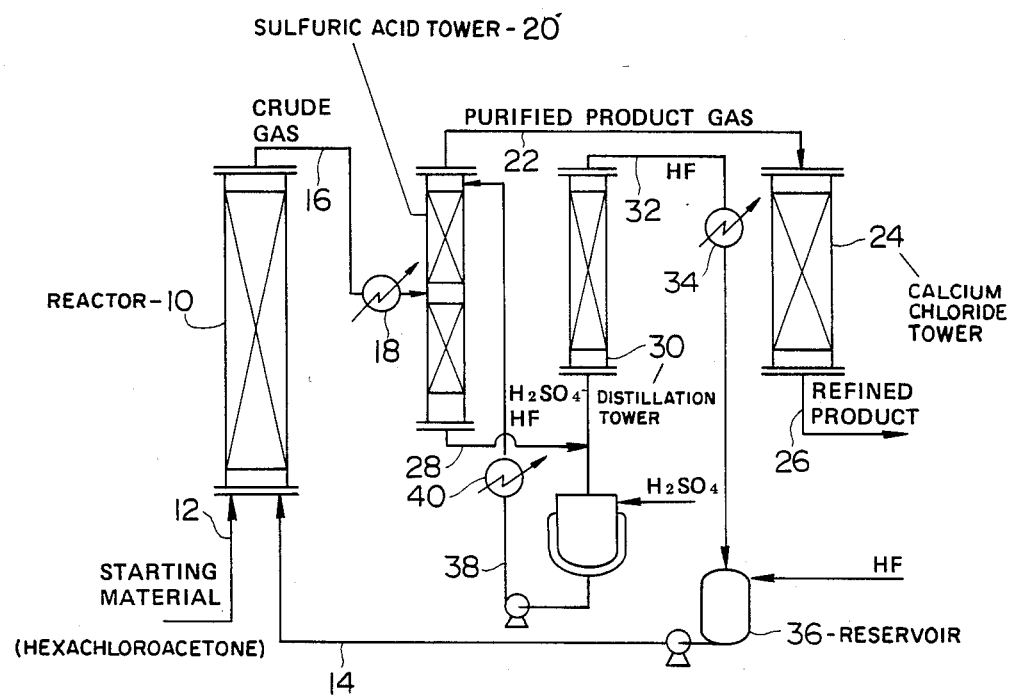

PROCESS OF PURIFYING FLUORINATED CARBONYL COMPOUND MIXED WITH HYDROGEN FLUORIDE

BACKGROUND OF THE INVENTION

This invention relates to a process of purifying a fluorinated carbonyl compound which is expressed by the general formula (I), and more particularly to a process of separating the fluorinated compound (I) from a crude product gas containing hydrogen fluoride together with the compound (I) while recovering hydrogen fluoride.

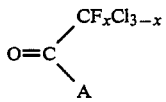
(I)

where x is 2 or 3 and A represents $CF_3$ or H.

Typical examples of fluorinated carbonyl compounds of the general formula (I) are hexafluoroacetone (abbreviated to HFA), pentafluorochloroacetone (referred to as 5FK) and trifluoroacetoaldehyde (abbreviated to TFA), and these compounds are all industrially important intermediate materials for fluorine-containing polymers, medicines, agricultural chemicals, solvents, heat transfer media, etc.

Various methods are known for the synthesis of such compounds (I), but a prevailing and probably most favorable method is a vapor phase fluorination reaction between hydrogen fluoride HF and a chlorinated carbonyl compound, such as a perhaloacetone, which is taken as a precursor. The reaction is carried out at 300°–400° C. using a suitable catalyst such as chromium oxide. By this method a desired compound (I) can be obtained easily and with high yield, on condition that HF is used in great excess of a theoretical quantity, usually in a quantity two to three times the theoretical quantity. Furthermore, it has been proposed to increase the quantity of HF in the aforementioned reaction to about 4.5 times the theoretical quantity with a view to realizing very stable and long-lasting operating conditions. The use of a large excess of HF in the fluorination reaction results in the presence of a large amount of HF in the gaseous product of the reaction. Accordingly it becomes a matter of importance to separate HF from the fluorinated carbonyl compound.

The fluorinated carbonyl compounds (I) are known to form stable complexes with HF, as shown below by way of example:

(a) heptafluoroisopropanol (decomposition point 14°–16° C.) from HFA and HF,

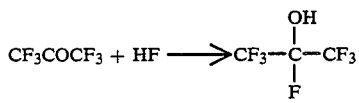

(b) hexafluorochloroisopropanol (decomposition point 32°–33° C.) from 5FK and HF,

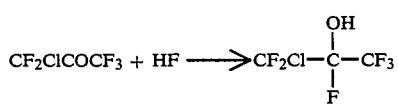

(c) 2-(1-chlorohexafluoroisopropoxy)-1-chloropentafluoroisopropanol (decomposition point −1° C.) from 5FK and HF,

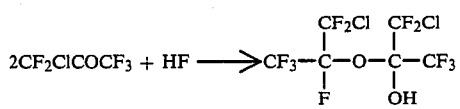

(d) tetrafluoro ethanol (b.p. 38° C. at 780 mmHg) from TFA and HF,

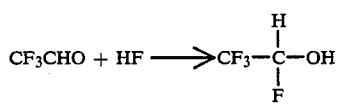

These complexes are stable compounds having relatively high decomposition points. At temperatures above the decomposition point of each complex, the gaseous product of the aforementioned fluorination reaction becomes an equilibrium mixture of the fluorinated compound (I), its HF complex and free HF. Therefore, a process of purifying the fluorinated compound (I) needs to include sole steps for the decomposition and/or separation of the complex.

In general, it is known to remove HF from the gaseous product of a fluorination reaction using excess HF by contact of the crude product gas with an inorganic fluoride such as NaF or $CaF_2$ which adsorbs HF, and also it is known to remove HF by using a reaction between HF and an alkaline earth metal salt such as $CaCO_3$ or $CaCl_2$. However, neither of these methods is suited for industrial purification of the fluorinated compounds (I) because of needing large-scale purification apparatus. Besides, in the case of the latter method it is impossible to recover HF for reuse in the fluorination reaction.

Some different kinds of methods have been proposed for the decomposition and separation of the above described complexes. In one method, the gas containing the HF complex is absorbed in water to decompose the complex and hydrate the organic components, and then HF existing in free state is neutralized with an alkali salt such as NaOH or $Na_2CO_3$, followed by filtration to separate precipitated NaF. For the purification of the fluorinated compounds (I) this method is uneconomical because HF cannot be recovered and also because a portion of the compound (I) tends to decompose during the purifying procedure. In another method the complex is forced to react with sulfur trioxide in order to separate HF as fluorosulfonic acid, and in a still different method the complex is forced to react with acetic anhydride in order to separate HF as acetyl fluoride. However, these two methods are unsuited to the recovery of HF gas and disadvantageous in using sulfur trioxide or acetic anhydride which is expensive and inconvenient for handling.

It is well known that concentrated sulfuric acid absorbs HF readily and largely but scarcely dissolves HCl therein. Using such properties of sulfuric acid, it has been proposed (e.g. Japanese Patent Application Publication No. 42(1967)-10202) to remove HF coexisting with a gaseous reaction product by absorption of HF in sulfuric acid.

SUMMARY OF THE INVENTION

It is an object of the present invention to provide an efficient and economical process of purifying a fluorinated carbonyl compound of the formula (I) coexisting with HF in a mixed gas without leaving any complex of the compound (I) with HF in the purified product and with recovery of most of HF contained in the mixed gas.

This invention provides a process of purifying a fluorinated carbonyl compound which is expressed by the general formula (I) as defined hereinbefore and coexists with hydrogen fluoride in a mixed gas. The purifying process comprises the steps of (a) adjusting the temperature of the mixed gas so as to remain in the range from 100° to 300° C., (b) bringing the mixed gas of which the temperature is in the above specified range into contact with concentrated sulfuric acid of which the temperature is maintained in the range from 10° to 40° C. to allow the sulfuric acid to absorb substantially the entire amount of hydrogen fluoride contained in the mixed gas, (c) recovering the unabsorbed portion of the mixed gas, and (d) recovering hydrogen fluoride absorbed in sulfuric acid.

Apparently the purifying method according to the invention utilizes the fact that sulfuric acid is a good absorbent for HF. The primary feature of the invention resides in that the crude mixed gas subject to purification is kept in a sufficiently heated state until its contact with sulfuric acid, whereas the sulfuric acid is maintained at a relatively low temperature.

The fluorinated cmpounds (I) form stable complexes with HF most readily at temperatures around room temperature, and such complexes easily dissolve in sulfuric acid and, therefore, cannot be separated from HF by a simple absorption process using sulfuric acid. However, we have confirmed that when maintained at temperatures above 100° C. (inclusive), and preferably above 150° C. (inclusive) in the presence of free HF the aforementioned complexes readily and completely undergo decomposition as represented by the following equation.

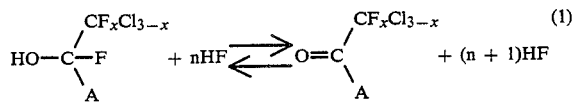

where x is 2 or 3, A represents $CF_3$ or H, and n is 0 (zero) or an integer between 1 and 10.

Conveniently the compounds of the formula (I) scarcely dissolve in sulfuric acid in themselves, whereas HF liberated by the decomposition of the complexes is entirely absorbed in sulfuric acid. Furthermore, we have confirmed that the compounds of the formula (I) do not form HF complexes while being in contact with sulfuric acid which is maintained at 10°–40° C. and contains a relatively large amount of HF. That is, in the purifying process of the invention the crude mixed gas is brought into contact with sulfuric acid while practically no portion of the fluorinated compound (I) is combined with HF, so that the removal of almost the entire amount of HF by absorption in sulfuric acid can be achieved without accompanied by the absorption or dissolution of the fluorinated compound (I) in sulfuric acid.

It is easy to recover HF absorbed in sulfuric acid by subsequent distillation. The refining process of the invention can be performed as a continuous process following the fluorination process to form the compound (I), and in that case HF recovered in the purifying process can be recycled to the fluorination process. Therefore, the purifying process of the invention is very favorable also from an economical point of view.

BRIEF DESCRIPTION OF THE DRAWING

The single FIGURE is a flow chart showing a continuous purifying process according to the invention.

DESCRIPTION OF THE PREFERRED EMBODIMENTS

The detail of the purifying process according to the invention will be described with respect to a continuous process illustrated in the FIGURE by way of example. A fluorinated compound of the formula (I) subject to purification is prepared in a reactor 10 by a known fluorination reaction between a chlorinated compound, such as hexachloroacetone in the case of preparing HFA, supplied via line 12 and HF gas supplied via line 14.

Via line 16 a crude product gas consisting of the fluorinated compound (I), a complex of the fluorinated compound (I) with HF, hydrogen chloride and excess HF is passed to a heat exchanger 18, where the gas temperature is adjusted so as to become in the range from 100° to 300° C., and preferably from 150° to 250° C. In the heated crude gas, the complex decomposes into the intended fluorinated compound (I) and HF as represented by the reaction of Equation (1). If the crude gas is not sufficiently heated the decomposition of the complex remains incomplete to result in that the recovery of the fluorinated compound (I) remains at a low level. However, it is unnecessary and uneconomical to raise the gas temperature beyond 300° C., and it is preferable to avoid heating over 250° C., because such excessive heating does not lead to further enhancement of the recovery of the intended compound (I).

The hot crude gas is introduced into a sulfuric acid tower 20 in which concentrated sulfuric acid is maintained at temperatures in the range from 10° to 40° C. During contact of the hot crude gas with the low temperature sulfuric acid in the tower 20, the excess HF present in the crude gas is almost entirely absorbed in the sulfuric acid. Therefore, the gas flowing out of the sulfuric acid tower 20 by an outlet at the tower top is almost free of HF. Via line 22 this gas is passed to a calcium chloride tower 24, where a trace amount of residual HF is completely removed from the gas. Line 26 extending from the calcium chloride tower 24 indicates the passage of the refined gas of the intended compound (I) to a recovery station such as a hydration tower (not shown).

Meanwhile, sulfuric acid used for the absorption of HF is discharged from a bottom section of the tower 20 and, via line 28, passed to a distillation tower 30 for recovery of HF by a customary distillation method. Via line 32 the recovered HF is returned to a reservoir tank 36 after condensation in a cooler 34. From this tank 36 extends the line 14 for supplying HF to the fluorination reactor 10, so that the recovered HF is recyled. The sulfuric acid separated from HF in the distillation tower 30 is returned via line 38 to the sulfuric acid tower 20 after cooling in a cooler 40. It is preferable that the concentration of HF in the recycled sulfuric acid is not higher than 6% by weight from the consideration of the relationship between the concentration of HF in sulfuric acid and the efficiency of absorption of HF in sulfuric acid.

By the above described purifying process it is possible to recover almost the entire amount of the intended compound (I) in refined state. At the same time HF is also recovered to the extent of about 96% recovery or more, and the recovered HF can be recycled. Accordingly this process is very favorable from an economical point of view, too.

EXPERIMENT 1

An experiment was carried out to examine solubilities of HF and HFA maintained at different temperatures in sulfuric acid.

First, a mixed gas consisting of 0.45 mole of HF and 0.35 mole of HFA was uniformly heated to 30° C. and brought into good contact with 98% sulfuric acid which had been maintained at 30° C. The gas emerged from the sulfuric acid was collected by using a water trap maintained at 30° C. and analyzed to find the quantities of HF and HFA in the collected gas. The result is shown in the following Table 1, in which "distribution ratio" refers to the ratio of HF absorbed in sulfuric acid to HF contained in the initial mixed gas, and also to the ratio of HFA contained in the finally collected gas to HFA contained in the initial mixed gas.

Next, a mixed gas consisting of 0.39 mole of HF and 0.24 mole of HFA was uniformly heated to 190° C. and brought into good contact with 98% sulfuric acid maintained at 30° C. The treated gas was collected and analyzed in the above described manner. The result is shown in Table 1.

TABLE 1

| Gas Temp. (°C.) | Mixed Gas (mole) | | Absorption in Sulfuric Acid (mole) | | Recovered Gas (mole) | | Distribution Ratio (%) | |
|---|---|---|---|---|---|---|---|---|
| | HF | HFA | HF | HFA | HF | HFA | HF | HFA |
| 30 | 0.45 | 0.35 | 0.34 | 0.23 | 0.11 | 0.11 | 75.5 | 31.1 |
| 190 | 0.39 | 0.24 | 0.38 | 0.01 | 0.01 | 0.23 | 97.4 | 95.8 |

The experimental data shown on the upper line of Table 1 indicate that at temperatures around room temperature HFA forms a stable complex with HF, that the complex maintained at such temperatures easily dissolves in sulfuric acid, and that consequently only about a third portion of HFA contained in the initial mixed gas can be recovered after treatment with sulfuric acid. In contrast, when the mixed gas before treatment is sufficiently heated little HFA is absorbed in sulfuric acid because of the preceding decomposition of the complex, and therefore HFA can be recovered with very high yield. The data on the lower line of Table 1 indicate also that almost the entire amount of HF, including a portion liberated by the decomposition of the complex, is trapped in sulfuric acid when the temperature of the acid is fairly low, such as 30° C.

EXPERIMENT 2

This experiment was carried out to examine solubilities of HFA in a mixed liquid of sulfuric acid and HF at varying temperatures.

A mixed liquid was prepared by well mixing 75 g of HF with concentrated sulfuric acid (98%). The mixed liquid was cooled to −50° C., and 78 g of HFA was dissolved in the cooled liquid. Then the temperature of the mixed liquid was raised to 0° C., and the liquid was left standing at this temperature for 1.5 hr. The gas developed from the liquid kept at 0° C. was collected and analyzed. After that the liquid temperature was raised to 20° C., and the liquid was left standing at this temperature for 1.5 hr to collect and analyze the gas developed from the liquid. The results are shown in Table 2.

TABLE 2

| Liquid Temp. (°C.) | Recovered Gas | | In Sulfuric Acid | |
|---|---|---|---|---|
| | HF | HFA | HF | HFA |
| 0 | 1 g | 70.0 g | 74 g | 8.0 g |
| 20 | — | 3.8 g | 74 g | 4.2 g |

The experimental data in Table 2 imply that 73.8 g of HFA (94.6% of HFA absorbed in the mixed liquid) could be recovered at 20° C. Thus, it was confirmed that in sulfuric acid HFA hardly forms a complex with HF even though the acid contains a large amount of HF and is kept at a relatively low temperature, i.e. at room temperature or somewhat below.

The invention will further be illustrated by the following nonlimitative examples.

EXAMPLE 1

To obtain HFA, hexachloroacetone was subjected to vapor phase contact reaction with HF at 350° C. using $CrF_3$ as catalyst. Purification of the crude product gas (of which the composition is shown in the following Table 3) was carried out generally in the manner as described hereinbefore with reference to the FIGURE, but the distillation tower 30 was disconnected from the sulfuric acid tower 20.

The crude product gas was maintained at 170° C. and, in that state, continuously introduced into the sulfuric acid tower for a total period of 1 hr. In the tower 20 concentrated sulfuric acid was maintained at 30° C. After that, the entire quantity of sulfuric acid was discharged from the sulfuric acid tower and transferred into the distillation tower to recover organic substances from the acid by distillation. Table 3 contains the compositions of the sulfuric acid discharged from the sulfuric acid tower, the gas recovered at the top of the sulfuric acid tower, sulfuric acid recovered in the distillation tower and the gas recovered from the distillation tower.

COMPARATIVE EXPERIMENT 1

The refining process of Example 1 was identically repeated except that the temperature of the crude product gas supplied to the sulfuric acid tower was 30° C. The analytical data obtained in this experiment are contained in Table 3.

TABLE 3

| | | HFA (kg) | 5FK (kg) | HF (kg) | HCl (kg) | $H_2SO_4$ (kg) |
|---|---|---|---|---|---|---|
| Ex. 1 (170° C.) | Crude Product Gas | 1.93 | 0.0858 | 1.160 | 2.63 | |
| | Sulfuric Acid after Use | — | — | 1.129 | — | 552.0 |
| | Gas at Top of Sulfuric Acid Tower | 1.93 | 0.0858 | 0.0314 | 2.63 | |
| | Sulfuric Acid after Distillation | — | — | 0.056 | — | 552.0 |
| | Gas Recovered by Distillation | — | — | 1.072 | — | |

TABLE 3-continued

|  |  | HFA (kg) | 5FK (kg) | HF (kg) | HCl (kg) | $H_2SO_4$ (kg) |
|---|---|---|---|---|---|---|
| Comp. Exp. 1 (30° C.) | Crude Product Gas | 1.74 | 0.0894 | 1.109 | 2.389 | |
| | Sulfuric Acid after Use | 1.343 | 0.0694 | 1.061 | — | 552.0 |
| | Gas at Top of Sulfuric Acid Tower | 0.400 | 0.0021 | 0.0482 | 2.389 | |

In example 1 the entire amount of HFA was recovered together with by-produced and useful 5FK, and the gas after the treatment with sulfuric acid contained only a very small amount of HF which could completely be removed in the calcium chloride tower 24. By the distillation, about 92% of HF initially present in the crude product gas was recovered.

In Comparative Experiment 1, about 77% of HFA and 5FK transferred from the crude product gas into sulfuric acid to result in failure to separate these organic materials from HF.

EXAMPLE 2

The process of Example 1 was revised to a continuous process as illustrated in the FIGURE.

The fluorination of HFA was carried out as described in Example 1, and the crude product gas (of which the composition is shown in Table 4) was maintained at 170° C. and, in that state, continuously introduced into the sulfuric acid tower 20 to make contact with sulfuric acid which was maintained at 30° C.

After the lapse of 3 hr from the start of the continuous purifying process, the compositions of gases sampled from the line 16 (crude product gas), line 22 (gas after treatment with sulfuric acid), line 26 (refined gas) and line 32 (HF recovered by distillation) were as shown in Table 4.

COMPARATIVE EXPERIMENT 2

The continuous purifying process of Example 2 was identically repeated except that the temperature of the crude product gas supplied to the sulfuric acid tower was 30° C. and that the analysis of the gases sampled from the lines 16, 22, 26 and 32 was performed after the lapse of 1 hr from the start of the refining process.

TABLE 4

|  |  | HFA (mole %) | 5FK (mole %) | HF (mole %) | HCl (mole %) |
|---|---|---|---|---|---|
| Ex. 2 (170° C.) | Line 16 | 8.7 | 0.27 | 38.6 | 52.4 |
| | Line 22 | 14.2 | 0.44 | $6 \times 10^{-5}$ | 85.4 |
| | Line 26 | 14.2 | 0.44 | 0 | 85.4 |
| | Line 32 | 0 | 0 | 100 | 0 |
| Comp. Exp. 2 (30° C.) | Line 16 | 7.96 | 0.37 | 42.0 | 49.6 |
| | Line 22 | 3.42 | 0.16 | 3.42 | 93.00 |
| | Line 26 | 3.42 | 0.16 | 0 | 96.42 |
| | Line 32 | 13.17 | 0.62 | 86.21 | 0 |

In Example 2 the entire amount of HFA was recovered together with by-produced 5FK, but in Comparative Experiment 2 the recovery of HFA remained only at 23%. Besides, in Comparative Experiment 2 a large amount of heat was generated in the calcium chloride tower 24.

EXAMPLE 3

To obtain TFA, trichloroacetoaldehyde was subjected to vapor phase contact reaction with HF at 260° C. using $CrF_3$ as catalyst. Purification of the crude product gas (of which the composition is shown in Table 5) was carried out as a continuous process generally in the manner as described with reference to the FIGURE.

The crude product gas was maintained at 170° C. and, in that state, continuously introduced into the sulfuric acid tower 20 to make contact with concentrated sulfuric acid which was maintained at 30° C. After the lapse of 4 hr from the start of the continuous purifying process, the compositions of gases sampled from the line 16 (crude product gas), line 22 (gas after treatment with sulfuric acid), line 26 (refined gas) and line 32 (HF recovered by distillation) were as shown in Table 5. As can be seen in Table 5, almost the entire amount of TFA was recovered.

TABLE 5

|  | TFA (mole %) | HF (mole %) | HCl (mole %) |
|---|---|---|---|
| Line 16 | 12.5 | 50.0 | 37.5 |
| Line 22 | 25.0 | 0.02 | 75.0 |
| Line 26 | 25.0 | 0 | 75.0 |
| Line 32 | 0 | 100 | 0 |

What is claimed is:

1. A process of purifying a fluorinated carbonyl compound which is expressed by the general formula

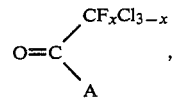

where x is 2 or 3 and A represents $CF_3$ or H, and coexists with hydrogen fluoride in a mixed gas, the process comprising the steps of:
 (a) adjusting the temperature of said mixed gas so as to remain in the range from 100° to 300° C.;
 (b) bringing said mixed gas of which the temperature is in said range into contact with concentrated sulfuric acid of which the temperature is maintained in the range from 10° to 40° C. to allow said sulfuric acid to absorb substantially the entire amount of hydrogen fluoride contained in said mixed gas;
 (c) recovering the unabsorbed portion of said mixed gas; and
 (d) recovering hydrogen fluoride absorbed in said sulfuric acid.

2. A process according to claim 1, wherein the temperature of said mixed gas at the start of step (b) is in the range from 150° to 250° C.

3. A process according to claim 1, further comprising the step of bringing the gas recovered at step (c) into contact with a calcium salt to remove any trace amount of hydrogen fluoride remaining in the recovered gas.

4. A process according to claim 1, wherein step (d) is carried out by distillation until the concentration of hydrogen fluoride in sulfuric acid becomes not more than 6% by weight, the process further comprising the step of recycling sulfuric acid after step (d) to step (b).

5. A process according to claim 1, wherein said fluorinated carbonyl compound is selected from the group consisting of hexafluoroacetone, pentafluorochloroacetone and trifluoroacetoaldehyde.

* * * * *

UNITED STATES PATENT AND TRADEMARK OFFICE
CERTIFICATE OF CORRECTION

PATENT NO. : 4,599,455

DATED : July 8, 1986

INVENTOR(S) : Yutaka MARUYAMA et al

It is certified that error appears in the above-identified patent and that said Letters Patent is hereby corrected as shown below:

On the title page, please insert the following item:

-- [73] Assignee: Central Glass Company, Limited
Ube City, Japan --

Signed and Sealed this

Seventeenth Day of March, 1987

Attest:

DONALD J. QUIGG

*Attesting Officer*   *Commissioner of Patents and Trademarks*